(12) United States Patent
Courtemanche et al.

(10) Patent No.: US 6,200,991 B1
(45) Date of Patent: Mar. 13, 2001

(54) IMIDAZOLE DERIVATIVES, PREPARATION AND THERAPEUTIC APPLICATION THEREOF

(75) Inventors: Gilles Courtemanche, Saint Martin du Tertre; Gérard DeFosse, Paris; Olivier Crespin, Cergy; Philippe Bovy, Mareil Marly, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/554,138

(22) PCT Filed: Nov. 17, 1998

(86) PCT No.: PCT/FR98/02446

§ 371 Date: Jun. 19, 2000

§ 102(e) Date: Jun. 19, 2000

(87) PCT Pub. No.: WO99/25710

PCT Pub. Date: May 27, 1999

(30) Foreign Application Priority Data

Nov. 19, 1997 (FR) .................................................. 97 14486

(51) Int. Cl.$^7$ ........................ A61K 31/454; A61P 43/00; C07D 401/12

(52) U.S. Cl. ......................... 514/326; 514/304; 514/305; 546/125; 546/135; 546/274.4; 546/210; 546/199

(58) Field of Search ................................ 546/210, 274.4, 546/125, 135, 199; 514/326, 304, 305

(56) References Cited

FOREIGN PATENT DOCUMENTS

| 282133 | 9/1988 | (EP) . |
|---|---|---|
| 449187 | 10/1991 | (EP) . |
| 2 747 678 | 10/1997 | (FR) . |
| WO 98/04546 | 2/1998 | (WO) . |

OTHER PUBLICATIONS

Tong et al., Journal of Medicinal Chemistry, vol. 39, No. 2, pp. 380–387 (1996).
Villalobos et al., Journal of Medicinal Chemistry, vol. 37, No. 17, pp. 2721–2734 (1994).
Derwent Patent Abstract No. 199813 (1998).
Derwent Patent Abstract No. 199751 (1997).

*Primary Examiner*—Joseph K. McKane
*Assistant Examiner*—Andrea M. D'Souza
(74) *Attorney, Agent, or Firm*—Michael D. Alexander

(57) ABSTRACT

A compound of formula (I)

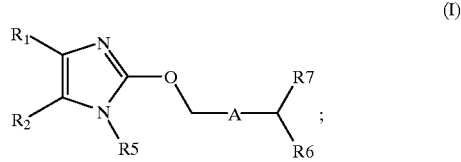

the process of preparing compounds of formula (I), their pharmaceutical compositions, and the method of treating diseases associated with $M_3$ muscarinic and/or $S-HT_4$ serotoninergic receptors.

16 Claims, No Drawings

IMIDAZOLE DERIVATIVES, PREPARATION AND THERAPEUTIC APPLICATION THEREOF

This application is a 371 of PCT/FR98/02446 filed Nov. 17, 1998.

The subject of the present invention is imidazole derivatives of general formula (I)

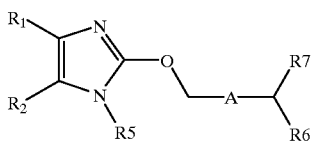

(I)

in which:

A represents a saturated or unsaturated heterocycle comprising a nitrogen atom of formula (B), (D), (E) or (F):

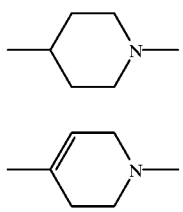

(B)

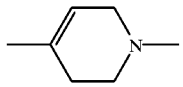

(D)

(E)

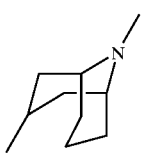

(F)

$R_1$ and $R_2$ represent, independently of each other, a hydrogen, a $C_{1-6}$ alkyl group, or together form a polymethylene group —$(CH_2)_n$—, it being possible for n to take the values from 3 to 6, $R_5$ represents a phenyl or a 2-, 3- or 4-pyridine, the phenyl or the pyridine being substituted with $R_3$ and $R'_3$,
where $R_3$ and $R'_3$ represent, independently of each other, a hydrogen atom, a halogen atom, a hydroxyl, a $C_{1-4}$ alkyl or $C_{1-6}$ alkoxy group, $R_6$ represents a phenyl or a 2-, 3- or 4-pyridine, the phenyl or the pyridine being substituted with $R_4$ and $R'_4$,
where $R_4$ and $R'_4$ represent, independently of each other, a hydrogen atom, a halogen atom, a hydroxyl, an amino, a cyano, a sulphonamide, an aminocarbonyl, a trifluoromethyl, a $C_{1-6}$-alkoxy, (di)hydroxy-$C_{1-6}$ alkoxy or $C_{1-4}$ alkyl group, and $R_7$ represents a hydrogen atom or a $C_{1-2}$ alkyl group.

Among these, the preferred compounds according to the invention are the compounds for which: A represents a piperidine (B), more especially A represents a piperidine (B) and $R_5$ represents a phenyl.

Among the latter, the compounds for which $R_6$ also represents a phenyl and $R_7$ represents a hydrogen are even more particularly preferred.

Within the framework of the present invention, there is understood by:

$C_{1-z}$, where z may take the values between 2 and 6, a carbon chain which may have from 1 to z carbon atoms, alkyl, a linear or branched saturated aliphatic group; for example, a $C_{1-6}$ alkyl group represents a linear or branched carbon chain of 1 to 6 carbon atoms, or preferably of 1 to 6, and more particularly consists of a methyl, ethyl, propyl, isopropyl, butyl, isobutyl, tert-butyl, and the like;

alkoxy, an alkyloxy group with a linear or branched saturated aliphatic chain, and halogen atom, a fluorine, a chlorine, a bromine or an iodine.

The compounds of general formula (I) may exist in the form of a free base, N-oxide or of addition salts with pharmaceutically acceptable acids, which also form part of the invention.

The compounds of general formula (I) comprise one or more asymmetric carbon atoms. They may therefore is exist in the form of enantiomers or diastereoisomers. These enantiomers, diastereoisomers, as well as mixtures thereof, including the racemic mixtures, form part of the invention.

The compounds of the invention can be prepared by processes illustrated in the schemes which follow, for which the operating conditions are routine for persons skilled in the art.

Scheme 1

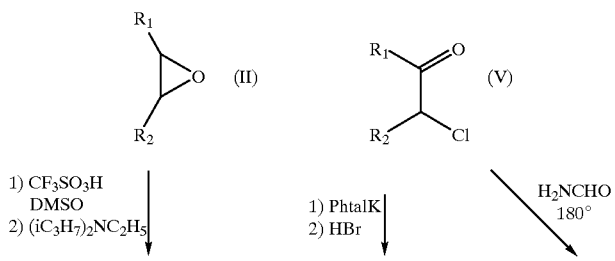

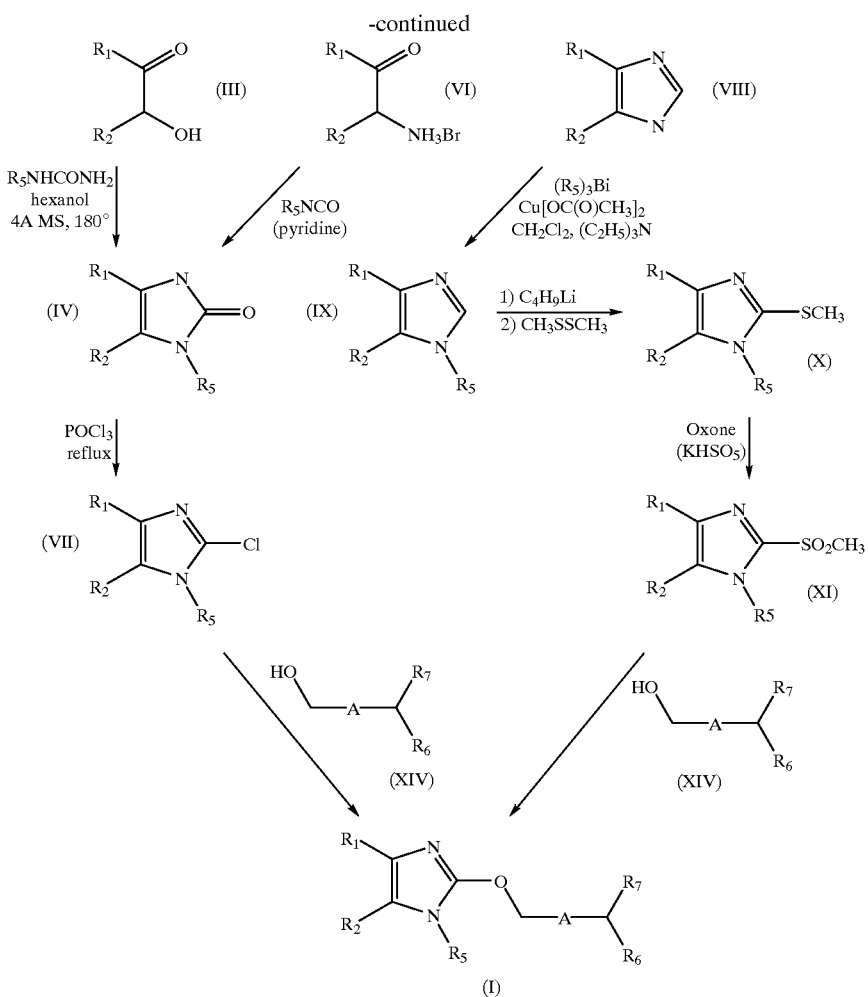

An epoxide of formula (II) is reacted successively with triflic acid in dimethyl sulphoxide and then with diisopropylethylamine to give the hydroxyketone (III) according to the method described by B. M. Trost in Tetrahedron letters 29, (18) 2163–66 (1988).

The hydroxyketone (III) is reacted with an arylurea ($R_5NHCONH_2$) at 180° C. in hexanol, optionally in the presence of a molecular sieve, to give the imidazolone (IV).

This imidazolone (IV) can also be obtained from the alpha-haloketone (V), by successive reactions of potassium phthalimide (PhthalK) and then of concentrated hydrobromic acid and of acetic acid, to give, first of all, the hydrobromide of the aminoketone (VI) which, by treatment with a phenylisocyanate ($R_5NCO$) in pyridine or dimethylformamide, gives the compound (IV).

Alternatively, the imidazolone (IV) may be prepared as indicated in Scheme 2 according to the method described in U.S. Pat. No. 3,432,520.

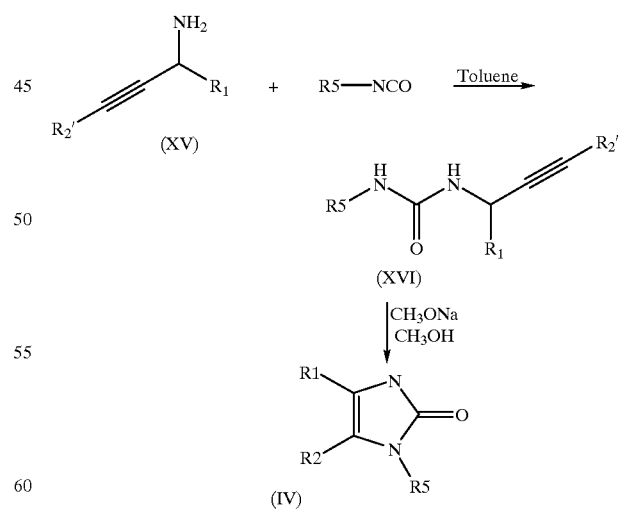

A propargylamine of formula (XV), in which $R_1$ is as defined above and $R'_2$ represents $R_2$ minus a carbon atom ($R_2=R'_2-(C\equiv)-$), is reacted with a phenylisocyanate ($R_5-NCO$) in toluene to give the urea (XVI) which, by treatment with an alkali metal alcoholate, such as sodium methoxide or ethoxide or potassium tert-butoxide, in the corresponding alcohol, causes an allenic rearrangement followed by cyclization to give the imidazolone (IV).

The imidazolone (IV) is then heated at the reflux temperature of phosphorus oxichloride, optionally in the presence of phosphorus pentachloride or of gaseous hydrochloric acid, to give the chloroimidazole (VII).

The condensation of the chloroimidazole (VII) with an alcohol of formula (XIV), in which A, $R_6$ and $R_7$ are as defined above, is carried out by the prior action of a non-nucleophilic base such as sodium hydride on this alcohol, followed by the reaction with the chloroimidazole in dimethylformamide at temperatures of between 20 and 120° C. (oil bath or microwave oven) to give the compounds of formula (I).

Alternatively, the compounds of formula (I) may be obtained from an alpha-haloketone of formula (V) which is thermally condensed with formamide to give the imidazole (VIII).

This imidazole (VIII) is then subjected to the action of a triarylbismuth (($R_5)_3$Bi) in the presence of copper acetate and of triethylamine in dichloromethane to give the imidazole (IX).

The proton at the 2-position of this imidazole (IX) is then removed by means of butyllithium in tetrahydrofuran at temperatures of between −78 and −10° C. The anion thus formed is trapped by means of dimethyl disulphide to give the sulphide (X).

Alternatively, the sulphides of formula (X) and more particularly those for which $R_2$ is a hydrogen atom may be obtained according to the Scheme 3.

Scheme 3

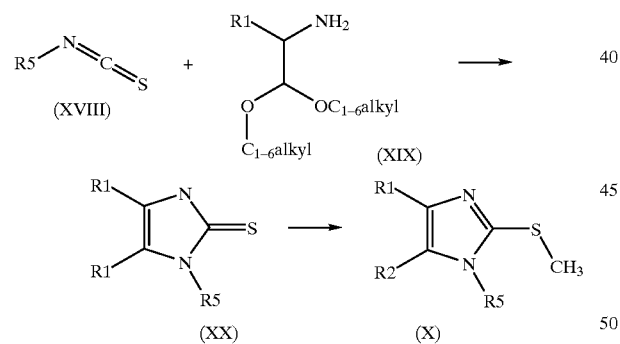

The isothiocyanate of formula (XVIII) is brought into contact, in an organic solvent such as toluene or dichloromethane, with a dialkyl acetal of formula (XIX) to give, in an intermediate phase, a thiourea which is cyclized into an imidazolinethione of formula (XX) by heating in an aqueous solution (0.01 to 12 N) of hydrochloric acid. The imidazolinethione of formula (XX) may be S-methylated by the successive action of sodium hydride and of methyl iodide in dimethylformamide at temperatures of between −20° C. and 60° C., to give the compound of formula (X), or alternatively by the action of methanol in hydrochloric acid at temperatures of between 20° C. and the reflux temperature.

The sulphide (X) is oxidized into a sulphone (XI) by the action of Oxone® (potassium peroxymonosulphate) in the presence of moist alumina. However, other oxidizing agents may be used, such as hydrogen peroxide or potassium permanganate in acetic acid.

The condensation of the sulphone (XI) with an alcoholate, formed by the action of a non-nucleophilic base such as sodium hydride on the alcohol of formula (XIV), is carried out in dimethylformamide at temperatures of between 20 and 120° C., to give the compounds of formula (I).

Alternatively, the compounds of formula (I), in which $R_6$ is a phenyl, $R_4=H$ and $R'_4=H$, can be modified in order to give other derivatives of formula (I) as indicated in Scheme 4.

Scheme 4

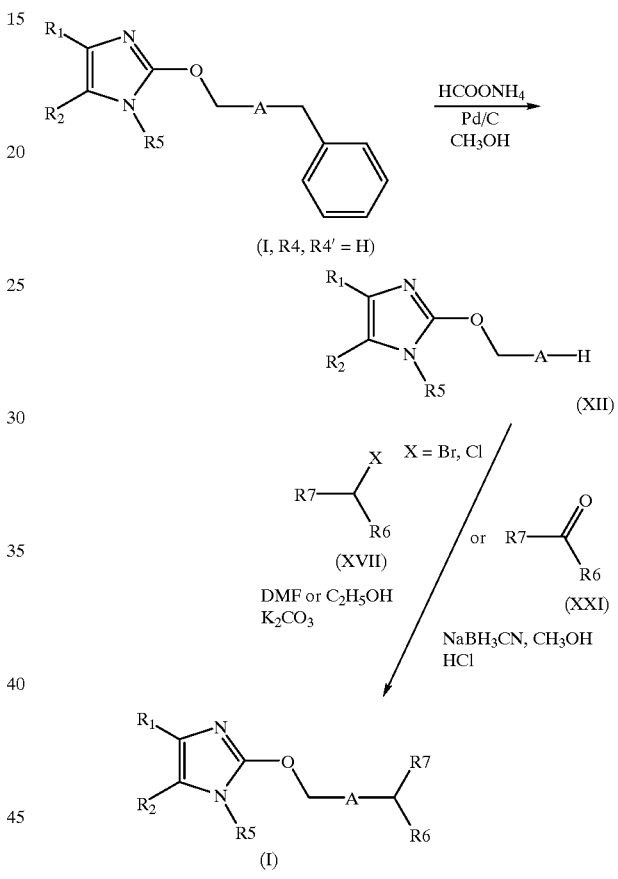

The compounds of formula (I), in which $R_6$ represents a phenyl, $R_4$ and $R'_4=H$ are debenzylated by the action of ammonium formate at the reflux temperature of methanol in the presence of a catalytic quantity of palladium on carbon, to give the derivative (XII).

The compounds of formula (XII) may then be reacted with an aryl halide of formula (XVII, $R_6$=phenyl or pyridyl in which $R_4$ and $R'_4$ may be different from a halogen) in the presence of a proton-accepting amine or of an inorganic base such as potassium carbonate, or by reductive amination by means of an aldehyde of formula (XXI, $R_6$ being as defined above) in the presence of hydrochloric acid or of sodium cyanoborohydride in methanol, to give the compounds of formula (I), in which $R_4$ and/or $R'_4$ do not represent a hydrogen.

In the case where ($R_4$ and/or $R'_4$) and/or ($R_3$ and/or $R'_3$) is a derivatizable functional group, it may be optionally oxidized, reduced, alkylated or dealkylated by conventional methods known to persons skilled in the art.

The compounds of formula (XIV) are commercially available or may be synthesized according to methods known to persons skilled in the art.

For example, the compound of formula (XIV), in which A represents a piperidine, and $R_6$ and $R_7$ are as defined above, may be obtained according to Scheme 5.

Scheme 5

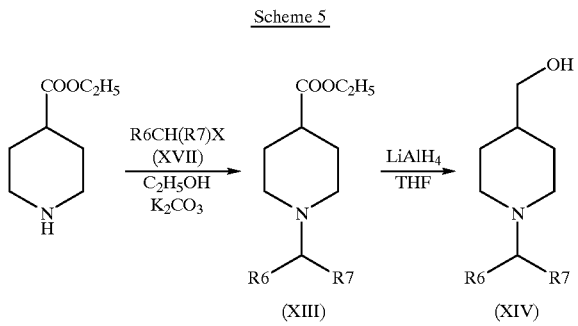

Ethyl isonipecotate is alkylated with the compound of formula (XVII), as defined above, to give the ester (XIII) which is reduced with the mixed hydride of lithium and aluminium to give the alcohol (XIV), according to methods known to persons skilled in the art. According to another example, the compound of formula (XIV), in which A represents an unsaturated heterocycle of formula (D), and $R_6$ and $R_7$ are as defined above, may be obtained according to Scheme 6.

Scheme 6

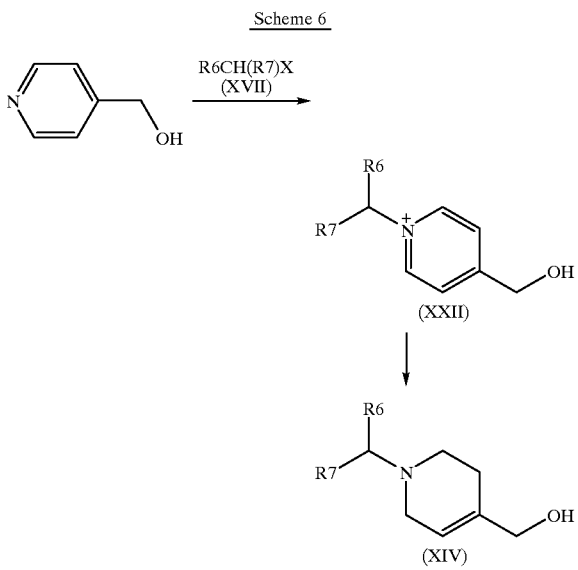

According to this scheme, 4-pyridinemethanol is reacted with the halide of formula (XVII), in toluene under reflux. The compound of formula (XXII) thus obtained is then reduced, in the presence for example of sodium borohydride in ethanol, to give the compound (XIV).

The compounds of formula (XIV), in which A represents a heterocycle of formula (E) or (F), and $R_6$ and $R_7$ are as defined above, may be obtained according to the method described by W. Schneider (Ger. Arch. Pharm., 308(5), 365–75 (1975)).

The other raw materials are directly available commercially, are described in the literature or can be synthesized by conventional methods known to persons skilled in the art.

The following examples illustrate the processes and techniques used for the preparation of this invention, without however limiting the scope of the invention. The elemental microanalysis and the NMR and IR spectra confirm the structures of the compounds obtained.

EXAMPLE 1

2-hydroxycyclohexanone 9.8 g (0.1 mol) of cyclohexene oxide in 75 ml of dimethyl sulphoxide are cooled on an ice bath, and a solution of 9 ml (0.1 mol) of triflic acid in 25 ml of dimethyl sulphoxide is added over 30 minutes. The mixture is allowed to return to room temperature and stirred for a further 2 hours. 150 ml of dichloromethane are added, the mixture is cooled to −78° C. and 87 ml (0.5 mol) of diisopropylethylamine are added over 30 minutes. The mixture is allowed to return to room temperature, stirred for a further 1 hour and poured over 1500 ml of a 10% solution of sodium bisulphate. The mixture is extracted with dichloromethane, dried over $MgSO_4$ and then evaporated. The residual oil is purified by flash chromatography on silica, eluting with methylene chloride, and 4.5 g of product are recovered. Yield=39.5%.

EXAMPLE 2

1-phenyl-4,5,6,7-tetrahydro-2H-benzimidazol-2-one

A mixture of 4.5 g (39.4 mmol) of 2-hydroxycyclohexanone, 7.5 g (55 mmol) of phenylurea and 7 ml of hexanol is stirred under reflux for 20 hours. The mixture is concentrated under vacuum and the solid residue is recrystallized from acetone, and 2.5 g of product, m.p.=220° C., are recovered. Yield—29.6%.

EXAMPLE 3

2-aminocyclohexanone hydrobromide

Following the procedure of D. Y. Curtin (J.Am. Chem. Soc. 77, 1105–10 (1955)), a mixture of 50 g (0.27 mol) of potassium phthalimide, 50 g (0.27 mol) of 2-chlorocyclohexanone and 200 ml of dimethylformamide is stirred at 95° C. for 8 hours. The mixture is poured over ice-cold water, ether is added and the mixture is stirred until crystallization of 2-phthalimidocyclohexanone is obtained. The product is drained, washed with water and with ether, and dried under vacuum. 40 g of the compound are obtained (m.p.=155° C.). A mixture of 40 g (0.16 mol) of the preceding derivative in 200 ml of acetic acid and 200 ml of 48% hydrobromic acid is then stirred under reflux for 4 hours. The mixture is cooled on an ice bath, the phthalic acid filtered and the product is concentrated under vacuum. The evaporation residue is taken up in 100 ml of ethanol and 100 ml of toluene and then concentrated under vacuum. This operation is repeated until a well-crystallized residue is obtained. It is taken up in a 50:50 alcohol/ether mixture filtered and dried under vacuum. 20 g of product are obtained. Yield=64% (m.p.=153° C.).

EXAMPLE 4

1-phenyl-4,5,6,7-tetrahydro-2H-benzimidazol-2-one

A mixture of 1.94 g (0.01 mol) of 2-aminocyclohexanone hydrobromide, 1.19 g (0.01 mol) of phenyl isocyanate and 4 ml of pyridine is stirred at 125° C. for 4 hours. Water is added, the mixture is stirred until crystallization is obtained, drained, washed with water and dried. The compound is purified by flash chromatography on silica, eluting with a 95:5 $CH_2Cl_2/CH_3OH$ mixture. 0.7 g of product is recovered. Yield=33% (m.p.=224° C.).

EXAMPLE 5

2-chloro-1-phenyl-4,5,6,7-tetrahydro-2H-benzimidazole

A mixture of 2.3 g (0.0107 mol) of 1-phenyl-4,5,6,7-tetrahydro-2H-benzimidazol-2-one and 30 ml of $POCl_3$ is stirred under reflux for 6 hours. The excess $POCl_3$ is evaporated under vacuum and the residue is hydrolyzed with water and concentrated ammonium hydroxide. The mixture is extracted twice with methylene chloride, evaporated and the residue is purified by flash chromatography on silica with an 80:20 heptane/ethyl acetate eluent. 0.8 g of product is recovered. Yield=32.2%.

EXAMPLE 6

4,5,6,7-tetrahydro-2H-benzimidazole 400 ml of formamide are added to 50 g (0.377 mol) of 2-chlorocyclohexanone placed in a 1-liter three-necked flask and then the mixture is heated at 180° C. for 2 h 30 min. The medium, having returned to room temperature, is poured over a 1 N sodium hydroxide solution (380 ml). This medium is then placed in a continuous liquid-liquid extractor and extracted with 400 ml of ethyl acetate for 6 h. The organic phase is dried over $MgSO_4$, concentrated under vacuum and then purified on a silica column using a gradient (methanol from 5 to 10% in dichloromethane). 10.2 g of product are obtained in the form of a gum. Yield=22%.

EXAMPLE 7

1-phenyl-4,5,6,7-tetrahydro-2H-benzimidazole 250 mg (2 mmol) of 4,5,6,7-tetrahydrobenzimidazole, 1.1 g (2.5 mmol) of triphenylbismuth, 363 mg (2 mmol) of copper acetate and 203 mg (2 mmol) of triethylamine are stirred in 5 ml of dichloromethane at room temperature for 24 hours. 2 grams of silica are then added and then the medium is concentrated under reduced pressure. The powder obtained is deposited on a silica gel and the expected product is eluted with a dichloromethane/methanol/ammonium hydroxide (95/5/0.5) mixture. 315 mg (79.5%) of 1-phenyl-4,5,6,7-tetrahydro-2H-benzimidazole are obtained.

EXAMPLE 8

1-phenyl-2-methylthio-4,5,6,7-tetrahydro-1H-benzimdazole 2.36 g (12 mmol) of 1-phenyl-4,5,6,7-tetrahydro-1H-benzimidazole are placed in a 100-ml three-necked flask under nitrogen, 20 ml of tetrahydrofuran are added and then the mixture is cooled to −78° C. 9 ml (14.3 mmol) of a 1.6 N butyllithium solution in hexane are then slowly added. The mixture is stirred at −80° C. for 5 minutes and then the temperature is allowed to rise to −20° C. and the mixture is stirred for a further 45 minutes at this temperature. The reaction medium is then cooled to −80° C. and a solution of 2.24 g (24 mmol) of dimethyl disulphide diluted in 10 ml of tetrahydrofuran is introduced into it dropwise. When the addition is complete, the medium is allowed to return to room temperature. It is then cooled to 0° C. before gently introducing 15 ml of water and then 15 ml of ethyl acetate. The phases are separated and then the aqueous phase is extracted twice with 10 ml of ethyl acetate. The combined organic phases are washed twice with 10 ml of water, once with 5 ml of brine and then dried over $MgSO_4$ and concentrated under vacuum. The crude reaction product is purified on a silica gel using, as eluting solution, a methanol gradient from 1 to 2% in dichloromethane. 2.17 g of 1-phenyl-2-methylthio-4,5,6,7-tetrahydrobenzimidazole are obtained. Yield=74% (m.p.=112° C.).

EXAMPLE 9

1-phenyl-2-methylsulphonyl-4,5,6,7-tetrahydro-1H-benzimidazole 3.8 g of previously moistened alumina, 7.07 g (11.5 mmol) of oxone and 10 ml of chloroform are vigorously stirred. A solution of 0.9 g (3.7 mmol) of 1-phenyl-2-methylthio-4,5,6,7-tetrahydro-1H-benzimidazole, solubilized in 10 ml of chloroform, is added to this medium and then the stirring is continued while heating under reflux for 2 hours. The mixture is cooled to 0° C. and then filtered, the solid is rinsed with 10 ml of chloroform and 10 ml of a 9/1 $THF/CH_3OH$ mixture. The filtrate is concentrated under reduced pressure and then purified on a silica column with the aid of a 99/1 then 98/2 dichloromethane/methanol mixture. 0.65 g of product is obtained. Yield=62%.

EXAMPLE 10

1-phenyl-2-[[1-(phenylmethyl)piperidin-4-yl]methoxy]-4,5,6,7-tetrahydro-1H-benzimidazole fumarate 0.031 g (1.33 mmol) of sodium hydride at 60% and 0.25 g of 1-benzyl-4-piperidinemethanol are gradually heated to 70° C. in 0.5 ml of dimethylformamide until the evolution of hydrogen ceases. The mixture is cooled to 0° C. and 0.23 g (1 mmol) of 2-chloro-1-phenyl-4,5,6,7-tetrahydro-1H-benzimidazole dissolved in 0.5 ml of dimethylformamide is added. The mixture is heated at 100° C. for 10 hours, water is added and the compound is extracted with methylene chloride. After concentration, it is purified on silica gel with a 97:3:0.3 $CH_2Cl_2/CH_3OH/NH_4OH$ mixture. 0.15 g of a thick oil is recovered which is salified in the fumarate form in alcohol. Yield=19.6% (m.p.=102° C.)

EXAMPLE 11

1-phenyl-2-(piperidin-4-ylmethoxy)-4,5,6,7-tetrahydro-1H-benzimidazole 0.98 g (2.44 mmol) of 1-phenyl-[[1-(phenylmethyl)piperidin-4-yl]methoxy]-4,5,6,7-tetrahydro-1H-benzimidazole is suspended in 20 ml of methanol and supplemented successively with 1.54 g (2.44 mmol) of ammonium formate and 0.75 g of 10% palladium on carbon. The mixture is heated at boiling temperature for 1 hour, filtered and concentrated under vacuum. The product is taken up in 5 N sodium hydroxide, extracted with methylene chloride and dried over $Na_2SO_4$. After concentration, 0.55 g of product is recovered. Yield=72%.

EXAMPLE 12

1-phenyl-2-[[1-(3-hydroxyphenylmethyl)piperidin-4-yl]methoxy]-4,5,6,7-tetrahydro-1H-benzimidazole fumarate A mixture of 0.55 g (1.176 mmol) of 1-phenyl-2-(piperidin-4-ylmethoxy)-4,5,6,7-tetrahydro-1H- benzimidazole and 0.12 g (0.88 mmol) of 3-hydroxybenzyl chloride in 6 ml of dimethylformamide is stirred at 75° C. for 15 hours. It is poured over water, extracted with methylene chloride, dried over $Na_2SO_4$ and evaporated to dryness. The expected compound is purified on a silica gel, eluting with a 97:3:0.3 $CH_2Cl_2/CH_3OH/NH_4OH$ mixture. The fumarate is produced in alcohol. Yield=15% (m.p.=149° C.)

EXAMPLE 13

N-phenyl-N'-propargylurea 25 g (0.45 mol) of propargylamine dissolved in 80 ml of toluene are added dropwise to a suspension of 50 ml (0.45 mol) of phenyl isocyanate in 160 ml of toluene. The mixture is stirred for 1 h 30 min, the precipitate is filtered, washed with a small amount of toluene and then dried in a vacuum oven at 40° C. 70.7 g of product are obtained. (m.p.=133° C.).

EXAMPLE 14

1,3-dihydro-5-methyl-1-phenyl-2H-imidazol-2-one 0.8 ml of 5.35 N sodium methoxide is added to a suspension of 10 g (0.062 mol) of N-phenyl-N'-propargylurea in 140 ml of toluene. The mixture is heated at the reflux temperature for 4 hours. The solvent is evaporated and then the solid residue is taken up in acetone. The product precipitates, it is filtered, washed with a small amount of acetone and dried under vacuum at 50° C. 6 g of product are obtained. (m.p.=207° C.).

EXAMPLE 15

1-(2-hydroxyphenyl)-2-[[1-(phenylmethyl)piperidin-4-yl]methoxy]-1H-imidazole 2.7 ml of a solution of hydrochloric acid (0.5 N) in isopropanol are slowly added, at 0° C. to a solution of 0.5 g (1.32 mmol) of 1-(2-methoxyphenyl)-2-[[1-(phenylmethyl) piperidin-4-yl]methoxy]-1H-imidazole in 15 ml of dichloromethane. The solvents are removed by evaporation and then the product is taken up in 15 ml of dichloromethane. The solution is cooled to −15° C. and 1.05 ml of boron tribromide is slowly added. The reaction medium is stirred for 3 h 30 min while allowing the temperature to return to 20° C. The reaction mixture is poured over ice and sodium bicarbonate is added until a pH=8 is obtained. After separating upon settling out, the aqueous phase is extracted twice with ethyl acetate and the combined organic phases are washed with water and then with brine. The medium is dried over magnesium sulphate, filtered and concentrated. The expected compound is purified on a silica gel, eluting with a 99:1 to 93:7 $CH_2Cl_2/CH_3OH$ mixture. 0.355 g of product is obtained. (Yield 74%)

EXAMPLE 16

1-(2-methoxyphenyl)-2-methylthio-1H-imidazole 8.8 ml (0.065 mol) of aminoacetaldehyde-diethylacetal diluted in 15 ml of toluene are added, under nitrogen, to a solution of 10 g (0.065 mol) of 2-methoxyphenylisothiocyanate in 105 ml of toluene. The reaction mixture is stirred for 1 h 30 min at room temperature. 2.75 ml (0.030 mol) of hydrochloric acid at 35% are added and the mixture is stirred for 2 hours under reflux. The mixture is concentrated and water is added and the precipitate is triturated. The product is drained, washed with an ether/n-heptane mixture and dried over $P_2O_5$ overnight. 8.18 g of 1-(2-methoxyphenyl)imidazoline-2-thione are thus obtained.

A solution of 8.1 g (0.039 mol) of this 1-(2-methoxyphenyl)imidazoline-2-thione in 88 ml of dimethylformamide is added dropwise, under nitrogen at 0° C., to a suspension of 1.19 g (0.047 mol) of sodium hydride (95%) in 88 ml of anhydrous dimethylformamide. The reaction mixture is stirred for ¾ h at 0° C. 2.7 ml (0.043 mol) of methyl iodide previously diluted in 24 ml of dimethylformamide are added and the mixture is stirred for 1 hour at 0° C. The reaction mixture is poured over ice, extracted three times with ethyl acetate and washed twice with water and then with brine. The product is dried over magnesium sulphate, filtered and concentrated. 8.6 g of oil are obtained.

The table which follows illustrates the chemical structures and the physical properties of some compounds of formula (I) according to the invention.

TABLE

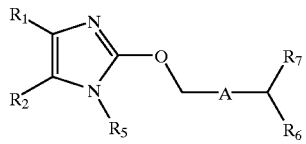

(I)

1) Compounds of formula (I) in which A = 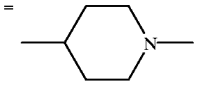

$R'_3 = R'_4 = $ —H, $R_5 = $ phenyl, $R_6 = $ phenyl, $R_7 = $ —H

| No. | $R_1$ | $R_2$ | $R_3$ | $R_4$ | m.p.(° C.) | Salt |
|---|---|---|---|---|---|---|
| 1 | $CH_3$ | $CH_3$ | H | H | 154 | Fumarate |
| 2 | —$(CH_2)_4$— | | H | H | 162 | Fumarate |
| 3 | —$(CH_2)_4$— | | 2-Cl | H | 155 | Fumarate |
| 4 | —$(CH_2)_4$— | | H | 3-OH | 149 | Fumarate |
| 5 | $CH_3CH_2$— | $CH_3CH_2$— | H | H | 148 | Fumarate |
| 6 | $CH_3$ | $CH_3$ | H | H | 119 | Fumarate |

TABLE-continued

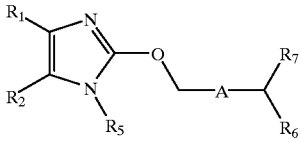
(I)

| No. | $R_1$ | $R_2$ | $R_4$ | $R'_4$ | m.p.(° C.) | Salt |
|---|---|---|---|---|---|---|
| 7 | $(CH_2)_2-$ H | $(CH_2)_2-$ H | H | H | 145 | Fumarate |
| 8 | $CH_3$ | $CH_3$ | 2-Cl | H | 133 | Fumarate |
| 9 | $-(CH_2)_6-$ | | H | H | 142 | Fumarate |
| 10 | H | $CH_3$ | H | H | 154 | Fumarate |
| 11 | $CH_3$ | $CH_3$ | 2-$CH_3$ | H | 134 | Fumarate |
| 12 | $CH_3$ | $CH_3$ | H | 3-OH | 138 | Fumarate |
| 13 | $CH_3$ | $CH_3$ | H | 3-$NH_2$ | 150 | — |
| 14 | $CH_3$ | $CH_3CH_2-$ | H | H | 138 | Fumarate |
| 15 | $CH_3CH_2-$ | $CH_3$ | H | H | 143 | Fumarate |
| 16 | H | H | 4-$OCH_3$ | H | 160 | Fumarate |
| 17 | $-(CH_2)_3-$ | | H | H | 157 | Fumarate |
| 18 | H | H | H | 3-OH | 129 | Fumarate |
| 19 | H | H | 4-OH | H | 140 | Fumarate |
| 20 | H | H | 2-$CH_3$ | H | 121 | Fumarate |
| 21 | H | H | 4-Cl | H | 179 | Fumarate |
| 22 | $(CH_3)_3C-$ | H | H | H | 97 | Fumarate |
| 23 | $CH_3$ | H | H | H | 98 | Fumarate |
| 24 | H | H | 2-Cl | H | 85 | Fumarate |
| 25 | $CH_3$ | $CH_3$ | H | 3-$CONH_2$ | 75 | Fumarate |
| 26 | H | H | 4-$CH_3$ | H | 170 | Fumarate |
| 27 | H | H | 4-F | H | 170 | Fumarate |
| 28 | $CH_3$ | H | H | 3-OH | 128 | Fumarate |
| 29 | $CH_3CH_2-$ | H | H | H | 140 | Fumarate |
| 30 | H | H | 2-$OCH_3$ | H | 132 | Fumarate |
| 31 | H | H | 3-$CH_3$ | H | 137 | Fumarate |
| 32 | H | H | 2-OH | H | 153 | Fumarate |
| 33 | H | H | 3-F | H | 132 | Fumarate |
| 34 | H | H | 3-$OCH_3$ | H | 141 | Fumarate |
| 35 | $CH_3CH_2-$ | H | H | 3-PH | 147 | Fumarate |
| 36 | H | H | 3-OH | H | 108 | Fumarate |
| 37 | $CH_3$ | $CH_3$ | H | 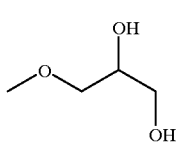 | 131 | Dibenzyl L-tartrate |
| 38 | H | H | H | 3-$SO_2NH_2$ | 172 | Fumarate |
| 39* | H | H | H | 3-$CH_3$ | 129 | Fumarate |
| 40* | H | H | H | 4-CN | 125 | Fumarate |
| 41 | H | H | 3-OH | 3-OH | — | — |

*In the same manner, the compounds for which $R_1$, $R_2$ and $R_3$ = H and $R_4$ = 2-$CH_3$, F, CN or $CF_3$; or 3-F, CN, $OCH_3$ or $CF_3$; or 4-$CH_3$, F, $OCH_3$ or $CF_3$ were synthesized.

2) Compounds of formula (I) in which A =

$R_3$ and $R'_3$ = —H, $R_5$ = phenyl, $R_6$ = phenyl, $R_7$ = —H.

| No. | $R_1$ | $R_2$ | $R_4$ | $R'_4$ | m.p.(° C.) | Salt |
|---|---|---|---|---|---|---|
| 42 | $CH_3$ | H | 3-OH | 4-OH | 161 | — |
| 43 | H | H | 2-F | 5-OH | 156 | Fumarate |
| 44 | H | H | 2-F | 5-$OCH_3$ | 149 | Fumarate |

3) Compounds of formula (I) in which A =

$R_4$ and $R'_4$ = H, $R_5$ = phenyl, $R_6$ = phenyl, $R_7$ = —H.

TABLE-continued (I)

| No. | R₁ | R₂ | R₃ | R'₃ | m.p.(° C.) | Salt |
|---|---|---|---|---|---|---|
| 45 | H | H | 3-OCH₃ | 5-OCH₃ | 155 | Fumarate |
| 46 | H | H | 3-OH | 5-OH | 125 | Fumarate |
| 47 | H | H | 2-OH | 5-OH | 132 | Fumarate |
| 48 | H | H | 2-OCH₃ | 5-OCH₃ | 110 | Fumarate |

4) Compounds of formula (I) in which A = (piperidine)

$R_5$ = pyridine, $R_6$ = phenyl, $R_7$ = —H.

| No. | R₁ | R₂ | R₃ | R'₃ | R₄ | R'₄ | R₅ | m.p.(° C.) | Salt |
|---|---|---|---|---|---|---|---|---|---|
| 49 | H | H | H | H | H | H | pyridin-3-yl | 144 | Fumarate |

5) Compounds of formula (I) in which A = (piperidine)

$R_5$ = phenyl, $R_7$ = —H.

| No. | R₁ | R₂ | R₃ | R'₃ | R₄ | R'₄ | R₆ | m.p.(° C.) | Salt |
|---|---|---|---|---|---|---|---|---|---|
| 50 | CH₃ | CH₃ | H | H | 3-CH₃ | H | pyridin-2-yl | 118 | Fumarate |
| 51 | CH₃ | CH₃ | H | H | H | H | pyridin-4-yl | 110 | Fumarate |
| 52 | CH₃ | CH₃ | H | H | H | H | pyridin-2-yl | 219 | Fumarate |
| 53 | CH₃ | CH₃ | H | H | H | H | pyridin-3-yl | 126 | Fumarate |

6) Compounds of formula (I) in which A = (bicyclic amine)

$R_5$ = phenyl, $R_6$ = phenyl, $R_7$ = —H.

| No. | R₁ | R₂ | R₃ | R'₃ | R₄ | R'₄ | m.p.(° C.) | Salt |
|---|---|---|---|---|---|---|---|---|
| 54 | —(CH₂)₄— | | H | H | H | H | 142 | Fumarate |

7) Compounds of formula (I) in which A = (tetrahydropyridine)

$R_5$ = phenyl, $R_6$ = phenyl, $R_7$ = —H.

| No. | R₁ | R₂ | R₃ | R'₃ | R₄ | R'₄ | m.p.(° C.) | Salt |
|---|---|---|---|---|---|---|---|---|
| 55 | H | H | H | H | H | H | 128 | Fumarate |

8) Compounds of formula (I) in which A = (piperidine)

$R_5$ = phenyl, $R_6$ = phenyl, $R_7$ = —CH₃.

| No. | R₁ | R₂ | R₃ | R'₃ | R₄ | R'₄ | m.p.(° C.) | Salt |
|---|---|---|---|---|---|---|---|---|
| 56 | CH₃ | H | H | H | H | H | 130 | Fumarate |

The compounds of the invention have been the subject of pharmacological trials which have shown their benefit as therapeutically active substances.

They have in particular been tested as regards their inhibitory effects on the binding of [$^3$H]-N-methylscopolamine to the $M_3$ type human muscarinic receptors transfected into CHO cells (Chinese hamster ovarian cells) (Buckley et al., Mol. Pharmacol. 35: 469–476, 1989). Membranes of CHO cells, in solution in a 10 mM TRIS-HCl, 2 mM EDTA buffer, pH 7.2, expressing the subtype of human muscarinic receptor $M_3$, were provided by the company Receptor Biology (Baltimore, USA).

10 to 30 μg of membranes were incubated in a phosphate buffer, pH 7.4 (Sigma, St Louis, Mo.) in the presence of 0.5 nM [$^3$H]N-methylscopolamine (NEN-Dupont, Les Ulis, France) and of a compound of the invention, in a total volume of 1 ml. The nonspecificity of the binding was determined with 0.5 μM of atropine (Sigma, St Louis, Mo.). The incubation (60 min at 25° C.) was stopped by rapid filtration on Whatmann GF/B filters using a Brandel filtration device. The filters were washed three times with 4 ml of cold phosphate buffer, dried and the radioactivity was measured by liquid scintillation (Ultima Gold scintillant). The concentration of compound shifting the specific binding by 500% ($IC_{50}$) was used to calculate the Ki values based on the Cheng-Prusoff equation. The efficacy of each product studied is expressed by the negative logarithm of their Ki (pKi).

The $IC_{50}$ values for the compounds of the invention in relation to the $M_3$ receptors are between 1 and 350 nM.

The compounds of the invention were also studied for their antagonist effects on the $M_3$ receptor-mediated contractions of female rabbit detrusor. Female rabbits (New Zealand, 3–4 kg; supplier ESD), about 20 weeks old, were sacrificed by cervical dislocation and then exsanguinated. After opening the abdomen, the bladders were removed and placed rapidly in a Krebs bicarbonate solution having the composition (mM): NaCl: 114; KCl: 4.7; $CaCl_2$: 2.5; $MgSO_4$: 1.2; $KH_2PO_4$: 1.2; $NaHCO_3$: 25; ascorbic acid: 1.1; glucose: 11.7. Propranolol (1 μM), methysergide (1 μM), ondansetron (1 μM) and GR113808 (1 μM) were added to the Krebs in order to inhibit, respectively, the β-adrenergic receptors and the various subtypes of serotoninergic receptors $5-HT_1/5-HT_2$, $5-HT_3$ and $5-HT_4$. The bladders were cleaned, made fat-free and then each side was cut into two longitudinal pieces about 4 mm wide and 15 mm long. The tissues were then placed in 20 ml containers thermostatted to 37° C. under carbogen (95% $O_2$, 5% $CO_2$) aeration and were subjected to a basal tension of 1 g. The tension was measured by means of isometric gauges (Hugo Sacks, type 351) connected to couplers (Gould) which convert and amplify the responses which are plotted on 4-track potentiometric recorders (Gould) and connected to a data acquisition system (Jad, Notocord). An equilibration time of about 45 minutes was observed during which the Krebs is replaced and the basal tension rectified.

After an equilibration period of 30 minutes, an initial contraction was made with carbachol (1 μM), a potent muscarinic agonist. The tissues were then thoroughly rinsed and then, after another 30-minute equilibration period, the tissues were incubated for 30 minutes in the presence or otherwise of a compound of the invention to be studied (concentration 0.1 or 1 μM) before making a carbachol response-concentration series per interval of half a logarithm unit. The concentrations producing half the maximum effect ($EC_{50}$ (μM)) were calculated for each series (absence or presence of the compound to be studied), then the power of the compound to shift the carbachol response curve was determined by calculating the affinity of the antagonist (apparent $pA_2$ or $pK_B$) according to the method of Furchgott (Handbook of Experimental Pharmacology, 1972, 283–335).

The $pK_B$ values for the compounds of the invention are between 7 and 9.5.

The compounds of the invention were also studied in relation to their affinity towards the $5-HT_4$ receptors in the striatum of guinea pigs, according to the method described by Grossman et al., in Br. J. Pharmacol., 109, 618–624 (1993). 300 to 400 g guinea pigs (Hartley, Charles River) undergo euthanasia and their brains are removed. The striata are excised and frozen at −80° C. On the day of the experiment, the tissue is thawed at +4° C. in 33 volumes of 50 mM Hepes-NaOH buffer (pH=7.4 at 20° C.) and homogenized with the aid of a Polytron® mill. The homogenate is centrifuged for 10 minutes at 48,000×g, the pellet is recovered, it is resuspended and it is centrifuged again under the same conditions. The final pellet is suspended in Hepes-NaOH buffer (30 mg of fresh tissue/ml). This membrane suspension is used as it is. 100 μl of the membrane suspension is incubated at 0° C. for 120 minutes, in the presence of 0.1 nM [$^3$H]GR113808 (specific activity: 80–85 Ci/mmol), in a final volume of 1 ml of Hepes-NaOH buffer (50 mM, pH=7.4), in the absence or in the presence of the test compound. The incubation is stopped by filtration on Whatman GF/B® filters, previously treated with 0.1% polyethyleneamine, each tube is rinsed with 4 ml of buffer at 0° C. and the medium is filtered again. The radioactivity retained on the filters is measured by liquid scintigraphy. The nonspecific binding is determined in the presence of 30 μM serotonin. The specific binding represents 90% of the total radioactivity recovered on the filter. For each concentration of compound studied, the percentage of inhibition of the specific binding of [$^3$H]GR118808 and then the concentration of the test compound which inhibits 50% of the specific binding ($IC_{50}$) are determined.

The $IC_{50}$ values for the compounds of the invention are between 1 and 350 nM.

Finally, the compounds of the invention were studied in relation to their antagonist effects on the $5-HT_4$ receptors in the oesophagus of rats. Male Sprague-Dawley rats weighing 300 to 450 g are used. A fragment of about 1.5 cm of the terminal portion of the oesophagus is removed rapidly, the muscle layer is removed, the inner muscle mucous membrane is opened longitudinally, it is mounted in an isolated organ container containing a Krebs-Henseleit solution at 32° C., oxygenated by a carbogen stream (95% $O_2$ and 5% $CO_2$), and it is connected to an isometric transducer under a basal tension of 0.5 g. The compounds are studied at a concentration of 1 μM. Their capacity to shift the relaxation introduced by 5-HT (at concentrations of 0.1 nM) of the oesophageal tissue precontracted with 1 μM substance P is measured. The compounds of the invention are active in this test.

The results of the biological tests show that the compounds of the invention are antagonists of the $M_3$ muscarinic and $5-HT_4$ serotoninergic receptors. They can therefore be used in the treatment of irritable bowel syndrome, memory disorders, obstruction of the airways and bladder instabilities and in particular urinary urgency incontinence.

The compounds of the invention, in combination with appropriate, pharmaceutically acceptable excipients may be provided in any form suitable for oral or parenteral administration, such as tablets, sugar-coated tablets, gelatin capsules, capsules, oral or injectable suspensions or solutions, and may contain doses which allow administration of 0.1 to 50 mg/kg per day.

What is claimed is:

1. A compound of formula (I)

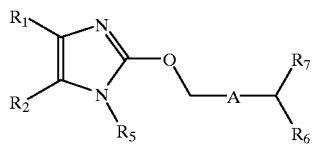

in which

A represents a saturated or unsaturated heterocycle of formula (B), (D), (E) or (F):

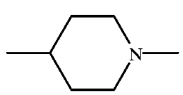

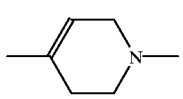

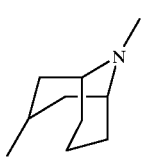

$R_1$ and $R_2$ represent, independently of each other, a hydrogen, a $C_{1-6}$ alkyl group, or together form a polymethylene group —$(CH_2)_n$—, it being possible for n to take the values from 3 to 6, $R_5$ represents a phenyl or a 2-, 3- or 4-pyridine, the phenyl or the pyridine being substituted with $R_3$ and $R'_3$,
wherein $R_3$ and $R'_3$ represent, independently of each other, a hydrogen atom, a halogen atom, a hydroxyl, a $C_{1-4}$ alkyl or $C_{1-6}$ alkoxy group, $R_6$ represents a phenyl or a 2-, 3-, or 4-pyridine, the phenyl or the pyridine being substituted with $R_4$ and $R'_4$,
wherein $R_4$ and $R'_4$ represent, independently of each other, a hydrogen atom, a halogen, a hydroxyl, an amino, a cyano, a sulphonamide, an aminocarbonyl, a trifluoromethyl, a $C_{1-6}$-alkoxy, (di)hydroxy-$C_{1-6}$ alkoxy or $C_{1-4}$ alkyl group, and $R_7$ represent a hydrogen atom or a C1-2 alkyl group, in the form of an enantiomer, a diastereoisomer or a mixture of these different forms, or an N-oxide thereof and their addition salts with pharmaceutically acceptable acids.

2. A compound according to claim 1 wherein A represents a piperidine (B) and $R_5$ represents a phenyl.

3. A compound according to claim 1 wherein the compound is chosen from the following compounds:
1-phenyl-2-[[1-(phenylmethyl)piperidin-4-yl]methoxy]-1H-imidazole;
1-(2-hydroxyphenyl)-2-[[1-(phenylmethyl)piperidin-4-yl]methoxy]-1H-imidazole;
1-(3-hydroxyphenyl)-2-[[1-(phenylmethyl)piperidin-4-yl]methoxy]-1H-imidazole;
1-phenyl-2-[[1-(3-hydroxyphenylmethyl)piperidin-4-yl]methoxy]-1H-imidazole;
1-phenyl-2-[[1-(2-fluoro-5-hydroxyphenylmethyl)piperidin-4-yl]methoxy]-1H-imidazole;
1-phenyl-2-[[1-(phenylmethyl)piperidin-4-yl]methoxy]-4,5-dimethyl-1H-imidazole;
1-phenyl-2-[[1-(3-hydroxyphenylmethyl)piperidin-4-yl]methoxy]-4,5-dimethyl-1H-imidazole;
1-phenyl-2-[[1-(phenylmethyl)piperidin-4-yl]methoxy]-4-methyl-1H-imidazole;
1-phenyl-2-[[1-(3-hydroxyphenylmethyl)piperidin-4-yl]methoxy]-4-methyl-1H-imidazole;
1-phenyl-2-[[1-(phenylmethyl)piperidin-4-yl]methoxy]-4-ethyl-1H-imidazole;
1-phenyl-2-[[1-(3-hydroxyphenylmethyl)piperidin-4-yl]methoxy]-4-ethyl-1H-imidazole; and
1-phenyl-2-[[1-(3-hydroxyphenylmethyl)piperidin-4-yl]methoxy]-4,5,6,7-tetrahydro-1H-benzimidazole, in the form of an enantiomer, a diastereoisomer or a mixture of these different forms, or an N-oxide thereof and their addition salts with pharmaceutically acceptable acids.

4. A process for the preparation of a compound according to claim 1 wherein a chloroimidazole of formula (VII)

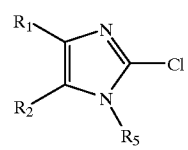

or a sulphone of formula (XI)

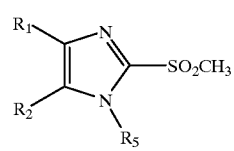

is reacted with an alcohol of formula (XIV),

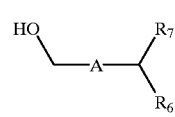

in which A, $R_6$ and $R_7$ are as defined in claim 1.

5. A pharmaceutical composition comprising a compound according to claim 1 and one or more pharmaceutically acceptable excipients.

6. A pharmaceutical composition comprising a compound according to claim 2 and one or more pharmaceutically acceptable excipients.

7. A pharmaceutical composition comprising a compound according to claim 3 and one or more pharmaceutically acceptable excipients.

8. A method for the treatment of diseases in which $M_3$ muscarinic and/or 5-$HT_4$ serotoninergic receptors are involved which comprises administering to a patient in need of such treatment an effective amount of a compound according to claim 1.

9. A method for the treatment of diseases in which $M_3$ muscarinic and/or 5-$HT_4$ serotoninergic receptors are involved which comprises administering to a patient in need of such treatment an effective amount of a compound according to claim 2.

10. A method for the treatment of diseases in which $M_3$ muscarinic and/or 5-$HT_4$ serotoninergic receptors are involved which comprises administering to a patient in need of such treatment an effective amount of a compound according to claim 3.

11. A method according to claim 8 for the treatment of irritable bowel syndrome, memory disorders, obstruction of the airways, and bladder instabilities.

12. A method according to claim 9 for the treatment of irritable bowel syndrome, memory disorders, obstruction of the airways, and bladder instabilities.

13. A method according to claim 10 for the treatment of irritable bowel syndrome, memory disorders, obstruction of the airways, and bladder instabilities.

14. A method according to claim 11 for the treatment of urinary incontinence.

15. A method according to claim 12 for the treatment of urinary incontinence.

16. A method according to claim 13 for the treatment of urinary incontinence.

* * * * *